United States Patent [19]

Napeloni et al.

[11] Patent Number: 4,843,896
[45] Date of Patent: Jul. 4, 1989

[54] PROBE FOR INTERNAL BORE INSPECTION

[75] Inventors: Paul Napeloni, Katy, Tex.; Daniel G. Sieber, Gadsden, Ala.; Thomas D. Cabe, Sugarland, Tex.

[73] Assignee: Western Stress, Inc., Houston, Tex.

[21] Appl. No.: 160,592

[22] Filed: Feb. 26, 1988

[51] Int. Cl.[4] ............................................. G01N 29/00
[52] U.S. Cl. .................................... 73/866.5; 166/241
[58] Field of Search .................... 73/866.5, 865.8, 618, 73/619, 620, 621, 622, 623, 592; 166/241

[56] References Cited

U.S. PATENT DOCUMENTS 4,218,923 8/1980 Triplett et al. ......................... 73/623
4,523,640 6/1985 Wilson et al. .................... 166/241 X

OTHER PUBLICATIONS

Harsonic ® Advertisement ©1986.

Primary Examiner—Jerry W. Myracle
Attorney, Agent, or Firm—Arnold, White & Durkee

[57] ABSTRACT

An inspection probe is disclosed that is capable of maintaining a constant orientation within a tubular vessel while inspecting the vessel. The probe includes at least one inspection mechanism disposed in a body. Two sets of three spring biased centering legs are disposed on each side of the body. The centering legs constantly maintain the probe on the same or parallel longitudinal axis as the vessel. A cable is attached to one end of the probe. The cable, together with the centering legs, assists in maintaining a constant axial orientation between the probe and vessel.

1 Claim, 2 Drawing Sheets

PROBE FOR INTERNAL BORE INSPECTION

BACKGROUND OF THE INVENTION

1. Field of the Invention

The present invention relates generally to inspection devices. More specifically, it relates to probes for inspection of the internal bore of pipes, tubes and other like vessels.

2. Background Art

Pipes, tubes and other like vessels (collectively "vessels") are used to hold and transport fluids. These fluids may include water, air, oil, natural gas and toxins. A defect in a vessel can be difficult to repair, expensive, harmful and cause delays. Thus, it is important to maintain the integrity of such vessels.

Inspection of the internal bore of vessels is helpful in maintaining the integrity of and locating defects in the vessel. Presently available inspection devices include fiber optic and ultrasonic probes. Usually the probes are fed into the vessel by cables and/or wires. Such presently available devices are not capable of maintaining a constant inspection orientation with the vessel.

Presently available probes have a tendency to twist inside the tubular vessel. Twisting affects the axial orientation. The probes will also rock inside the tubular vessel. Rocking affects the longitudinal orientation. Rocking is especially detrimental when using ultrasonic devices because maintaining a constant angle between the transducer and wall of a vessel is essential to obtaining accurate measurements. Thus, a need exists for an inspection probe capable of maintaining a constant inspection orientation with a vessel.

SUMMARY OF THE INVENTION

Briefly, the present invention comprises a probe having at least one inspection mechanism centrally disposed in a body. A front extension is connected to the front end of the body and at its other end to a cap. A first biasing means is disposed around the front extension and between the front end of the body and the cap. A back extension is connected at one end to the back end of the body and at its other end to a cable head. A second biasing means is disposed around the back extension and between the back end of the body and the cable head. Two sets of three centering legs are pivotally connected to the body. The first set is evenly disposed around the front end of the body and biased by the first biasing means. The second set is evenly disposed around the back end of the body and biased by the second biasing means.

Each centering leg of each set acts congruently and independent of the other set of centering legs. This feature coupled with the central location of the inspection mechanism assists in maintaining the probe in the same or parallel longitudinal axis with the vessel being inspected. This allows a constant inspection angle between the inspection mechanism and the bore of the vessel.

The cable connected to the cable head will bend but will not twist because it is phenolically connected to the head. As such, the probe is able to negotiate bends and the like in the vessel without affecting the axial orientation of the probe.

Maintaining a constant axial and longitudinal orientation provides several advantages not consistently accomplished by the prior devices. For instance, the number of ultrasonic inspection mechanisms ("transducers") can be increased because the "cross talk" caused by the shifting ("rocking or twisting") of the probe is reduced or eliminated. Also, the measurements are more accurate when the inspection angle is constantly maintained.

The components of the present invention are preferably connected mechanically rather than by welding or adhesives. This aspect facilitates repairs in the field. It also allows for the use of components composed of stainless steel or having a protective coating.

The centering legs are preferably biased by springs. This aspect facilitates the travel of the probe through vessels that change in diameter and/or contour ("curves"). The centering legs are easily changed to accommodate inspection of vessels having diameters outside of the range of the legs presently on the probe.

The features and aspects of the present invention mentioned are meant to be illustrative rather than exhaustive. Further features and aspects of the invention will become evident when reading the specification in view of the drawings.

DESCRIPTION OF THE PREFERRED EMBODIMENT

1. Components

Figure 1:
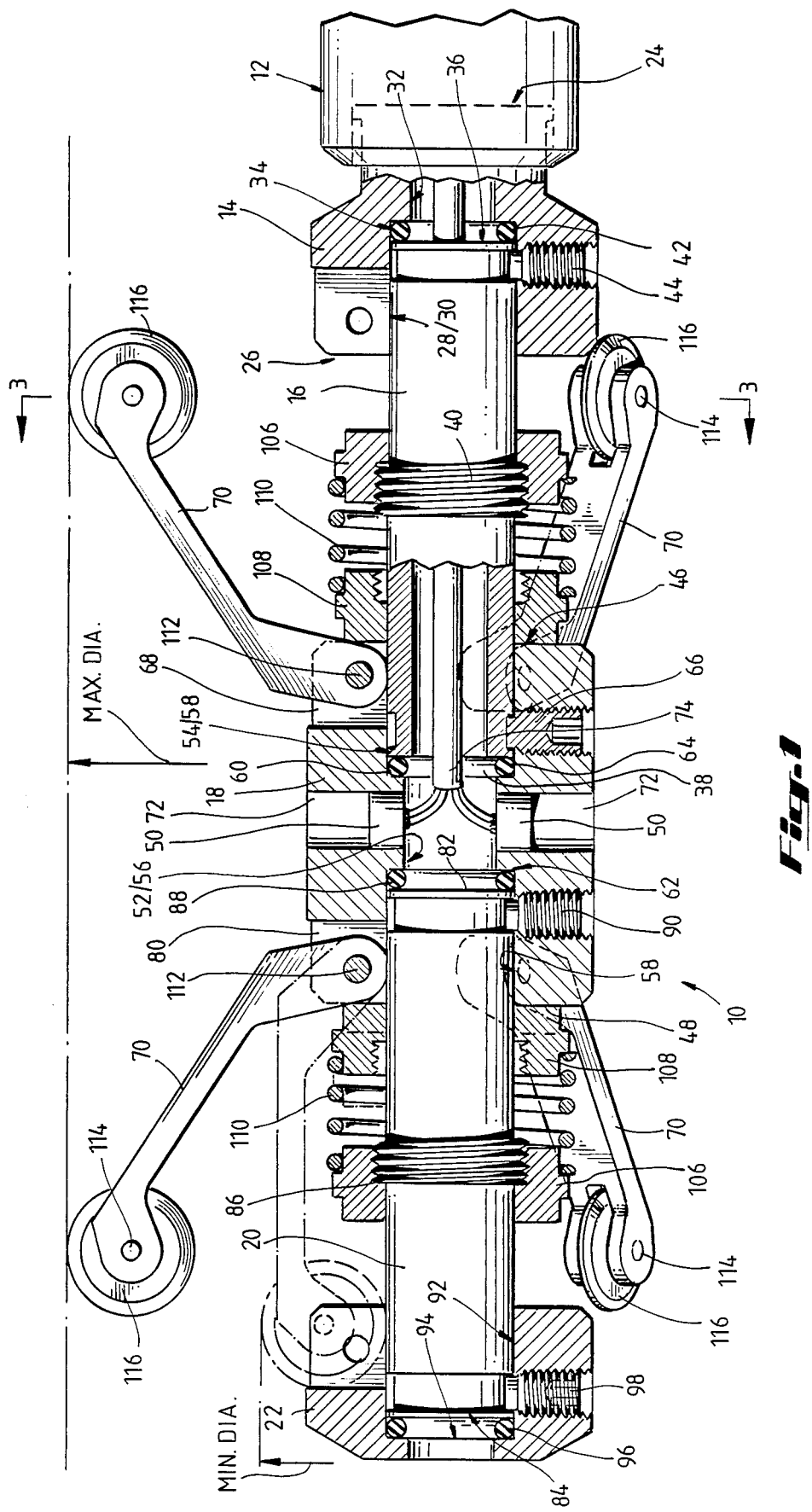
FIG. 1 is a side cross-sectional view of the present invention.
Figure 2:
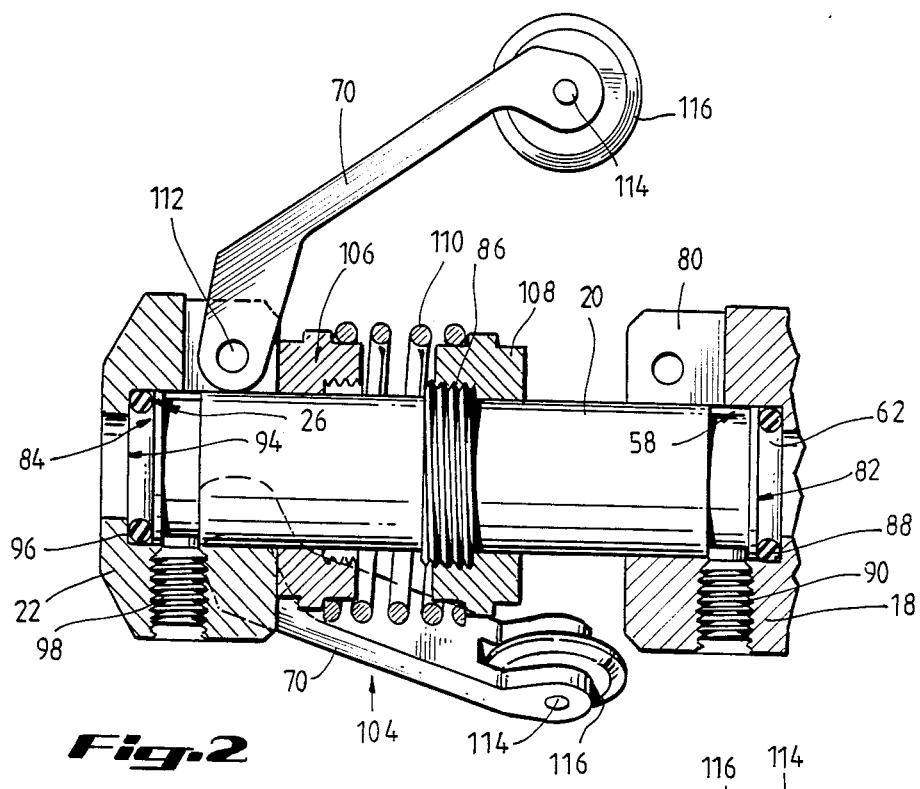
FIG. 2 is a partial cross-sectional side view of the present invention.
Figure 3:
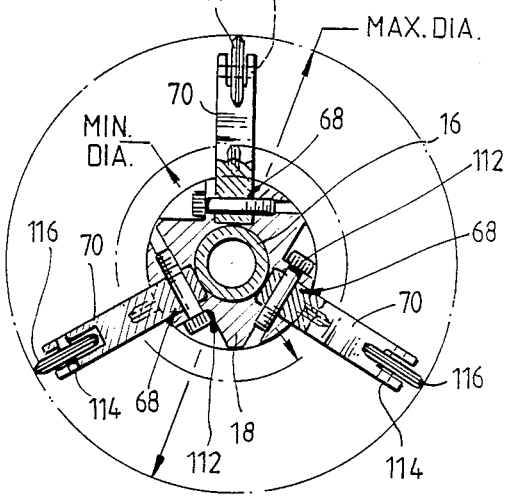
FIG. 3 is a frontal cross-sectional view of the present invention.

A probe 10 of the present invention is shown in FIGS. 1-4. The probe 10 is connected to a cable 12. The body components of probe 10 include a head 14, first extension 16, body 18, second extension 20 and cap 22.

Cable 12 is preferably a flexible, pressure tight multi-pin coaxial cable. Cable 12 is threaded through head 14 and first extension 16 and phenolically molded to head 14.

Head 14 is preferably composed of stainless steel and includes cable end 24, probe end 26 and bore 28. Bore 28 includes two tiers 30 and 32 and step 34. Cable end 24 and step 34 are adapted to receive cable 12. Cable 12 is phenolically molded to cable end 24 of head 14. Probe end 26 and tier 32 are adapted to receive first extension 16.

Preferably, first extension 16 is cylindrical, composed of stainless steel and includes ends 36 and 38 and threads 40. End 36 is sealed against step 34 of head 14 by o-ring 42 and connected to head 14 by set screws 44. End 38 is connected to body 18.

Preferably, body 18 is cylindrical, composed of stainless steel and includes ends 46 and 48, at least one port 50 and bore 52. Bore 52 includes tiers 54, 56 and 58 and steps 60 and 62.

End 46 and tier 54 of body 18 are adapted to receive end 38 of first extension 16. First extension 16 is sealed against step 60 by o-ring 64 and connected to body 18 by set screws 66. End 46 includes three equally spaced grooves 68 each adapted to receive a centering leg 70.

An inspection mechanism 72 is disposed in each port 50. Inspection mechanism 72 may include but is not limited to ultrasonic transducers, fiber optics, laser optics and television cameras. Preferably, the body 18 includes eight ports 50 disposed in the same axial plane to accommodate eight ultrasonic transducers 72.

A connector 74 is disposed in tier 56 of body 18. Connector 74 includes port leads 76 and body leads 78. Each port lead 76 is connected to a corresponding inspection mechanism 72. Each body lead 78 is connected to a corresponding lead in cable 12.

End 48 of body 18 includes three equally spaced grooves 80 each of which is adapted to receive a centering leg 70. End 48 and tier 58 of body 18 are adapted to receive second extension 20.

Preferably, second extension 20 is cylindrical, composed of stainless steel and includes ends 82 and 84 and threads 86. End 82 is sealed against step 62 of body 18 by o-ring 88 and connected to body 18 by set screws 90. Cap 22 is connected to end 84 of second extension 20.

Preferably, cap 22 is composed of stainless steel and includes a bore 92 and base 94. End 84 of second extension 20 is sealed against base 94 by o-ring 96 and connected to cap 22 by set screws 98.

A centering mechanism 100 is shown in FIGS. 1-4 and includes two assemblies 102 and 104. Each assembly includes three centering legs 70, one retaining ring 106, one actuation ring 108 and a biasing means 110.

Retaining rings 106, actuation rings 108 and biasing means 110 are all composed of stainless steel. Legs 70 are also composed of stainless steel and include ends 112 and 114. Preferably a wheel 116 is pivotally connected to each leg 70 at end 114.

Assembly 102 is disposed between end 46 of body 18 and threads 40 of extension 16. A leg 70 is pivotally connected at end 112 to each groove 68 on body 18. A retaining ring 106 is connected to extension 16 on threads 40. An actuation ring 108 is disposed on extension 16 between end 46 and retaining ring 106. A biasing means 110 is disposed around extension 16 between the retaining ring 106 and actuation ring 108.

Assembly 104 is disposed between end 48 of body 18 and threads 86 of extension 20. A leg 70 is pivotally connected at end 112 to each groove 80 on body 18. A retaining ring 106 is connected to extension 20 on threads 86. An actuation ring 108 is disposed on extension 20 between end 48 and retaining ring 106. A biasing means 110 is disposed around extension 20 between retaining ring 106 and actuation ring 108.

Probe 10 is connected to a means for reading (not shown) the output from the inspection mechanism 72 by the cable 12. Means for reading (or compiling) output from the inspection mechanism 72 includes, but is not limited to, an oscilloscope, computer or television monitor.

2. Operation

The probe 10 is threaded into a vessel 118 to be inspected by pushing it with cable 12. The probe 10 is then located, and the inspection mechanism 72 is actuated. The probe 10 is pulled through the vessel 118 while the inspection mechanism 72 takes continuous or incremental readings. The readings are transmitted through the cable 12 and compiled or displayed in the means for reading.

Figure 4:
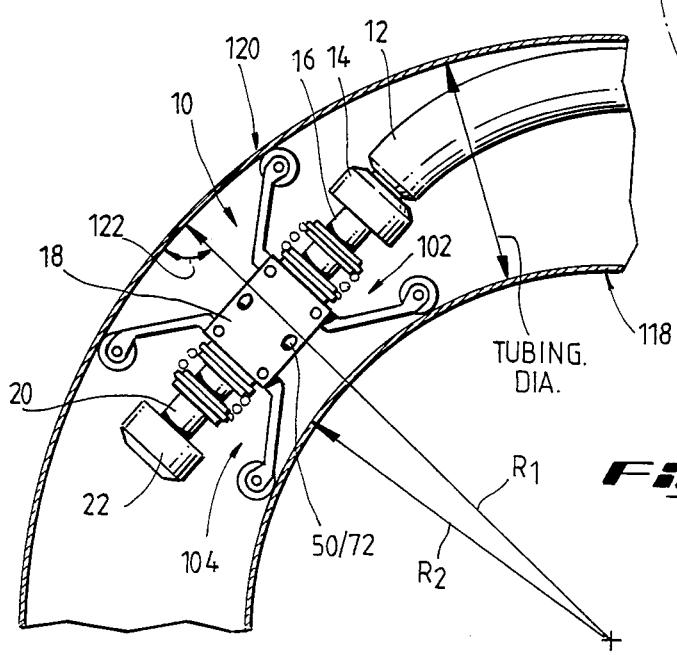
FIG. 4 is a view of the present invention negotiating a bend in a vessel.

FIG. 4 shows the probe 10 in a bend 120 in a vessel 118. The centering mechanism 100 maintains a constant orientation between the probe 10 and the vessel 118. In the case of the preferred embodiment where pressure transducers 72 are used, the centering mechanism 100 maintains a constant inspection angle 122 between the transducer 72 and the vessel 118.

What is claimed is:
1. An inspection probe comprising:
   a. a head;
   b. a first extension having a first end, second end and bore;
   c. the first end of the first extension is connected to the head;
   d. a body having a first end, a second end, at least one port, and a bore;
   e. the first end of the body is connected to the second end of the first extension;
   f. a second extension having a first end, second end and bore;
   g. the first end of the second extension is connected to the second end of the body;
   h. a cap connected to the second end of the second extension;
   i. three equally spaced grooves disposed in the first end of the body;
   j. three equally spaced grooves disposed in the second end of the body;
   k. a plurality of legs having a first end and a second end;
   l. one leg is connected to each of the grooves on the first and second end of the body at the first end of the leg;
   m. a wheel connected to each leg at the second end of each leg;
   n. a retaining ring disposed around and connected to each extension;
   o. an actuation ring disposed around each extension between the retaining ring and the corresponding end of the body;
   p. a biasing means disposed around each extension between the retaining ring and actuation ring; and
   q. an inspection mechanism disposed in each port.

* * * * *